(12) United States Patent
Frenken et al.

(10) Patent No.: US 7,196,187 B2
(45) Date of Patent: *Mar. 27, 2007

(54) METHOD FOR PRODUCING ANTIBODY FRAGMENTS

(75) Inventors: Leon Frenken, Bedford (GB); Cornelis P. van der Logt, Bedford (GB)

(73) Assignee: Unilever Patent Holdings B.V., Vlaardingen (NL)

(*) Notice: Subject to any disclaimer, the term of this patent is extended or adjusted under 35 U.S.C. 154(b) by 381 days.

This patent is subject to a terminal disclaimer.

(21) Appl. No.: 10/122,434

(22) Filed: Apr. 16, 2002

(65) Prior Publication Data

US 2003/0078402 A1    Apr. 24, 2003

Related U.S. Application Data

(62) Division of application No. 09/487,253, filed on Jan. 19, 2000, now Pat. No. 6,399,763.

(30) Foreign Application Priority Data

Jan. 19, 1999   (EP)   ................... 99300351

(51) Int. Cl.
C07H 21/04     (2006.01)
C12N 15/09     (2006.01)
(52) U.S. Cl. ................. 536/23.53; 536/23.1; 536/23.5; 435/440; 435/463; 435/320.1
(58) Field of Classification Search ............... 536/23.1, 536/23.53; 435/320.1, 91.4; 530/387.1, 530/387.3
See application file for complete search history.

(56) References Cited

FOREIGN PATENT DOCUMENTS

EP   584421 A1   3/1994
WO   WO 9425591 A1 * 11/1994

OTHER PUBLICATIONS

Davies J, Reichmann L, Single chain domains as small recognition units: design and in vitro antigen selection of camelized, human VH domains with improved protein stability, 1996, Protein Eng 9:531-537.*
Aujame et al. (1997), "High affinity human antibodies by phage display," Human Antibodies 8(4):155-168.
Davies et al. (1995), "Antibody VH domains as small recognition units," Bio/Technology 13(5):457-479.
Finnern et al. (1995), "Molecular characteristics of anti-self antibody fragments against neutrophil cytoplasmic antigens from human V gene phage display libraries," Clin Exp Immunol 102(3):566-574.
Ghahroudi et al. (1997), "Selection and identification of single domain antibody fragments from camel heavy-chain antibodies," FEBS Lett 414:521-526.
Hoogenboom et al. (1998), "Antibody phage display technology and its applications," Immunotechnology 4:1-20.
Nguyen et al. (1998), "The specific variable domain of camel heavy-chain antibodies is encoded in the germline," J Mol Biol 275:413-418.

* cited by examiner

Primary Examiner—Q. Janice Li
(74) Attorney, Agent, or Firm—Morgan, Lewis and Bockius; Christopher J. Betti

(57) ABSTRACT

An expression library comprising a repertoire of nucleic acid sequences cloned from a non-immunised source, each nucleic acid sequence encoding at least part of a variable domain of a heavy chain derived from an immunoglobulin naturally devoid of light chains (VHH) wherein the extent of sequence variability in the library is enhanced compared to the corresponding naïve expression library by introducing mutations in one or more of the complementarity determining regions (CDRs) of the nucleic acid sequences or by generating alternative combinations of CDR and framework sequences not naturally present in the naïve library repertoire. Also disclosed is the use of such a library in preparing antibodies, more particularly antibody fragments.

6 Claims, 6 Drawing Sheets

Step 1 : Framework regions

Step 2A

Step2B

Step2C

Step 3

Step 4

Step 5A

Step 5B

Step 5C

Step 5D

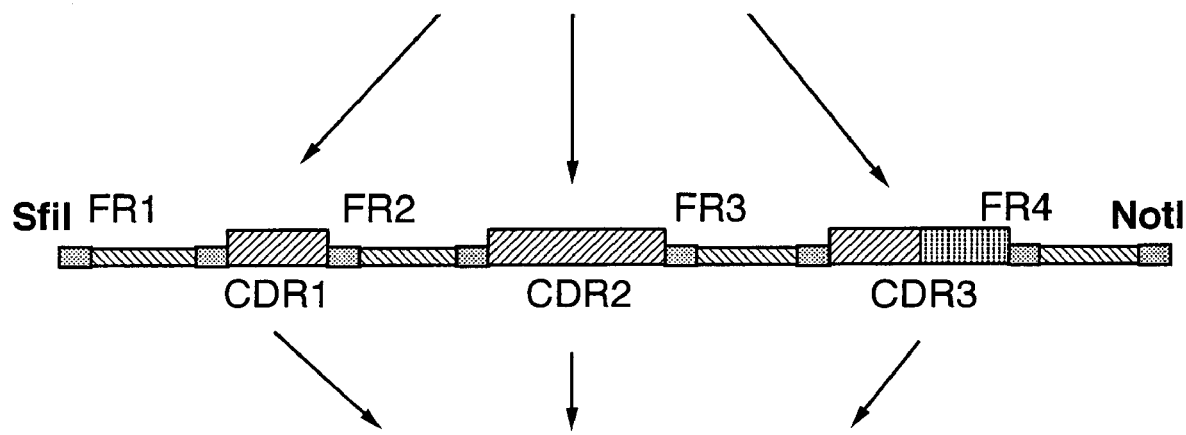

SEQUENCE LISTING

<160> NUMBER OF SEQ ID NOS: 39

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: PRIMER

<400> SEQUENCE: 1
aggtsmarct gcagsagtcw gg                                          22

<210> SEQ ID NO 2
<211> LENGTH: 57
<212> TYPE: DNA
<213> ORGANISM: Artificial Sequence
<220> FEATURE:
<223> OTHER INFORMATION: Description of Artificial Sequence: PRIMER

<400> SEQUENCE: 2
catgccatga ctcgcggccc agccggccat ggccsaggts marctgcags agtcwgg    57

```
<210> SEQ ID NO 3
<211> LENGTH: 53
<212> TYPE: DNA
<213> ORGANISM: Artificial Sequence
<220> FEATURE:
<223> OTHER INFORMATION: Description of Artificial Sequence: PRIMER

<400> SEQUENCE: 3
aacagttaag cttccgcttg cggccgcgga gctggggtct tcgctgtggt gcg            53

<210> SEQ ID NO 4
<211> LENGTH: 53
<212> TYPE: DNA
<213> ORGANISM: Artificial Sequence
<220> FEATURE:
<223> OTHER INFORMATION: Description of Artificial Sequence: PRIMER

<400> SEQUENCE: 4
aacagttaag cttccgcttg cggccgctgg ttgtggtttt ggtgtcttgg gtt            53

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: PRIMER

<400> SEQUENCE: 5
attgcctacg gcagccgctg                                                 20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: PRIMER

<400> SEQUENCE: 6
tccagaggct gcacaggaga                                                 20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: PRIMER

<400> SEQUENCE: 7
tggtwccgcc aggctccagg                                                 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: PRIMER

<400> SEQUENCE: 8
gcgacmaact cgcgctsctt                                                 20

<210> SEQ ID NO 9
<211> LENGTH: 20
<212> TYPE: DNA
<213> ORGANISM: Artificial Sequence
<220> FEATURE:
```

<223> OTHER INFORMATION: Description of Artificial Sequence: PRIMER

<400> SEQUENCE: 9
tggttccgcc aggccccagg                                                    20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: PRIMER

<400> SEQUENCE: 10
acatgagacc scctcrcgct c                                                  21

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: PRIMER

<400> SEQUENCE: 11
tatgcagact ccgtgaaggg ccg                                                23

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: PRIMER

<400> SEQUENCE: 12
acagtaatar acggccgtgt c                                                  21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: PRIMER

<400> SEQUENCE: 13
tggggccagg ggacccwggt c                                                  21

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: PRIMER

<400> SEQUENCE: 14
ttcagatcct cttctgagat gag                                                23

<210> SEQ ID NO 15
<211> LENGTH: 67
<212> TYPE: DNA
<213> ORGANISM: Artificial Sequence
<220> FEATURE:
<221> NAME/KEY: UNSURE
<222> LOCATION: 33, 34, 36, 37, 39, 40
<223> OTHER INFORMATION: any
<223> OTHER INFORMATION: Description of Artificial Sequence: PRIMER

<400> SEQUENCE: 15

-continued tytcctgtgc agcctctgga aghayyttba ghnnknnknn katgggttgg twccgccagg    60
ctccagg    67

<210> SEQ ID NO 16
<211> LENGTH: 67
<212> TYPE: DNA
<213> ORGANISM: Artificial Sequence
<220> FEATURE:
<221> NAME/KEY: UNSURE
<222> LOCATION: 33, 34, 39, 40
<223> OTHER INFORMATION: any
<223> OTHER INFORMATION: Description of Artificial Sequence: PRIMER

<400> SEQUENCE: 16
tytcctgtgc agcctctgga dtcayyttbg atnnktatnn kattggttgg ttccgccagg    60
ccccagg    67

<210> SEQ ID NO 17
<211> LENGTH: 71
<212> TYPE: DNA
<213> ORGANISM: Artificial Sequence
<220> FEATURE:
<221> NAME/KEY: UNSURE
<222> LOCATION: 22, 23, 31, 32, 40, 41, 46, 47
<223> OTHER INFORMATION: any
<223> OTHER INFORMATION: Description of Artificial Sequence: PRIMER

<400> SEQUENCE: 17
aagsagcgcg agttkgtcgc annkattwct nnkggtggtn nkacannkta tgcagactcc    60
gtgaagggcc g    71

<210> SEQ ID NO 18
<211> LENGTH: 74
<212> TYPE: DNA
<213> ORGANISM: Artificial Sequence
<220> FEATURE:
<221> NAME/KEY: UNSURE
<222> LOCATION: 22, 23, 31, 32, 34, 35, 43, 44, 49, 50
<223> OTHER INFORMATION: any
<223> OTHER INFORMATION: Description of Artificial Sequence: PRIMER

<400> SEQUENCE: 18
aagsagcgcg agttkgtcgc annkattwct nnknnkggtg gtnnkacann ktatgcagac    60
tccgtgaagg gccg    74

<210> SEQ ID NO 19
<211> LENGTH: 74
<212> TYPE: DNA
<213> ORGANISM: Artificial Sequence
<220> FEATURE:
<221> NAME/KEY: UNSURE
<222> LOCATION: 31, 32, 34, 35, 43, 44, 49, 50
<223> OTHER INFORMATION: any
<223> OTHER INFORMATION: Description of Artificial Sequence: PRIMER

<400> SEQUENCE: 19
gagcgygagg sggtctcatg ttgtattwct nnknnkgatg gtnnkacann ktatgcagac    60
tccgtgaagg gccg    74

<210> SEQ ID NO 20
<211> LENGTH: 57
<212> TYPE: DNA
<213> ORGANISM: Artificial Sequence
<220> FEATURE:
<221> NAME/KEY: UNSURE
<222> LOCATION: 28, 29, 31, 32
<223> OTHER INFORMATION: any
<223> OTHER INFORMATION: Description of Artificial Sequence: PRIMER

<400> SEQUENCE: 20
gacacggccg tytattactg trmtgccnnk nnktactggg gccaggggac ccakgtc       57

<210> SEQ ID NO 21
<211> LENGTH: 60
<212> TYPE: DNA
<213> ORGANISM: Artificial Sequence
<220> FEATURE:
<221> NAME/KEY: UNSURE
<222> LOCATION: 28, 29, 31, 32, 34, 35
<223> OTHER INFORMATION: any
<223> OTHER INFORMATION: Description of Artificial Sequence: PRIMER

<400> SEQUENCE: 21
gacacggccg tytattactg trmtgccnnk nnknnktact ggggccaggg gacccakgtc    60

<210> SEQ ID NO 22
<211> LENGTH: 63
<212> TYPE: DNA
<213> ORGANISM: Artificial Sequence
<220> FEATURE:
<221> NAME/KEY: UNSURE
<222> LOCATION: 28, 29, 31, 32, 34, 35, 37, 38
<223> OTHER INFORMATION: any
<223> OTHER INFORMATION: Description of Artificial Sequence: PRIMER

<400> SEQUENCE: 22
gacacggccg tytattactg trmtgccnnk nnknnknnkt actggggcca ggggacccak    60
gtc                                                                  63

<210> SEQ ID NO 23
<211> LENGTH: 66
<212> TYPE: DNA
<213> ORGANISM: Artificial Sequence
<220> FEATURE:
<221> NAME/KEY: UNSURE
<222> LOCATION: 28, 29, 31, 32, 34, 35, 37, 38, 40, 41
<223> OTHER INFORMATION: any
<223> OTHER INFORMATION: Description of Artificial Sequence: PRIMER

<400> SEQUENCE: 23
gacacggccg tytattactg trmtgccnnk nnknnknnkn nktactgggg ccagggggacc   60 cakgtc                                                               66

<210> SEQ ID NO 24
<211> LENGTH: 69
<212> TYPE: DNA
<213> ORGANISM: Artificial Sequence
<220> FEATURE:
<221> NAME/KEY: UNSURE
<222> LOCATION: 28, 29, 31, 32, 34, 35, 37, 38, 40, 41, 43, 44
<223> OTHER INFORMATION: any
<223> OTHER INFORMATION: Description of Artificial Sequence: PRIMER

<400> SEQUENCE: 24
gacacggccg tytattactg trmtgccnnk nnknnknnkn nknnktactg gggccagggg    60 acccakgtc                                                            69

<210> SEQ ID NO 25
<211> LENGTH: 72
<212> TYPE: DNA
<213> ORGANISM: Artificial Sequence

```
<220> FEATURE:
<221> NAME/KEY: UNSURE
<222> LOCATION: 28, 29, 31, 32, 34, 35, 37, 38, 40, 41, 43, 44, 46, 47
<223> OTHER INFORMATION: any
<223> OTHER INFORMATION: Description of Artificial Sequence: PRIMER

<400> SEQUENCE: 25
gacacggccg tytattactg trmtgccnnk nnknnknnkn nknnknnkta ctgggccag      60 gggacccakg tc                                                         72

<210> SEQ ID NO 26
<211> LENGTH: 75
<212> TYPE: DNA
<213> ORGANISM: Artificial Sequence
<220> FEATURE:
<221> NAME/KEY: UNSURE
<222> LOCATION: 28, 29, 31, 32, 34, 35, 37, 38, 40, 41, 43, 44, 46, 47,
      49, 50
<223> OTHER INFORMATION: any
<223> OTHER INFORMATION: Description of Artificial Sequence:  PRIMER

<400> SEQUENCE: 26
gacacggccg tytattactg trmtgccnnk nnknnknnkn nknnknnknn ktactggggc     60 cagggggaccc akgtc                                                     75

<210> SEQ ID NO 27
<211> LENGTH: 78
<212> TYPE: DNA
<213> ORGANISM: Artificial Sequence
<220> FEATURE:
<221> NAME/KEY: UNSURE
<222> LOCATION: 28, 29, 31, 32, 34, 35, 37, 38, 40, 41, 43, 44, 46, 47,
      49, 50, 52
<222> LOCATION: 53
<223> OTHER INFORMATION: any
<223> OTHER INFORMATION: Description of Artificial Sequence: PRIMER

<400> SEQUENCE: 27
gacacggccg tytattactg trmtgccnnk nnknnknnkn nknnknnknn knnktactgg     60
ggccagggga cccakgtc                                                   78

<210> SEQ ID NO 28
<211> LENGTH: 81
<212> TYPE: DNA
<213> ORGANISM: Artificial Sequence
<220> FEATURE:
<221> NAME/KEY: UNSURE
<222> LOCATION: 28, 29, 31, 32, 34, 35, 37, 38, 40, 41, 43, 44, 46, 47,
      49, 50, 52
<222> LOCATION: 53, 55, 56
<223> OTHER INFORMATION: any
<223> OTHER INFORMATION: Description of Artificial Sequence: PRIMER

<400> SEQUENCE: 28
gacacggccg tytattactg trmtgccnnk nnknnknnkn nknnknnknn knnknnktac     60
tggggccagg ggacccakgt c                                               81

<210> SEQ ID NO 29
<211> LENGTH: 84
<212> TYPE: DNA
<213> ORGANISM: Artificial Sequence
<220> FEATURE:
<221> NAME/KEY: UNSURE
<222> LOCATION: 28, 29, 31, 32, 34, 35, 37, 38, 40, 41, 43, 44, 46, 47,
      49, 50, 52
<222> LOCATION: 53, 55, 56, 58, 59
<223> OTHER INFORMATION: any
```

<223> OTHER INFORMATION: Description of Artificial Sequence: PRIMER

<400> SEQUENCE: 29
gacacggccg tytattactg trmtgccnnk nnknnknnkn nknnknnknn knnknnknnk     60
tactggggcc agggaccca kgtc                                             84

<210> SEQ ID NO 30
<211> LENGTH: 87
<212> TYPE: DNA
<213> ORGANISM: Artificial Sequence
<220> FEATURE:
<221> NAME/KEY: UNSURE
<222> LOCATION: 28, 29, 31, 32, 34, 35, 37, 38, 40, 41, 43, 44, 46, 47,
      49, 50, 52
<222> LOCATION: 53, 55, 56, 58, 59, 61, 62
<223> OTHER INFORMATION: any
<223> OTHER INFORMATION: Description of Artificial Sequence: PRIMER

<400> SEQUENCE: 30
gacacggccg tytattactg trmtgccnnk nnknnknnkn nknnknnknn knnknnknnk     60
nnktactggg gccaggggac ccakgtc                                         87

<210> SEQ ID NO 31
<211> LENGTH: 90
<212> TYPE: DNA
<213> ORGANISM: Artificial Sequence
<220> FEATURE:
<221> NAME/KEY: UNSURE
<222> LOCATION: 28, 29, 31, 32, 34, 35, 37, 38, 40, 41, 43, 44, 46, 47,
      49, 50, 52
<222> LOCATION: 53, 55, 56, 58, 59, 61, 62, 64, 65
<223> OTHER INFORMATION: any
<223> OTHER INFORMATION: Description of Artificial Sequence: PRIMER

<400> SEQUENCE: 31
gacacggccg tytattactg trmtgccnnk nnknnknnkn nknnknnknn knnknnknnk     60
nnknnktact ggggccaggg gacccakgtc                                      90

<210> SEQ ID NO 32
<211> LENGTH: 93
<212> TYPE: DNA
<213> ORGANISM: Artificial Sequence
<220> FEATURE:
<221> NAME/KEY: UNSURE
<222> LOCATION: 28, 29, 31, 32, 34, 35, 37, 38, 40, 41, 43, 44, 46, 47,
      49, 50, 52
<222> LOCATION: 53, 55, 56, 58, 59, 61, 62, 64, 65, 67, 68
<223> OTHER INFORMATION: any
<223> OTHER INFORMATION: Description of Artificial Sequence: PRIMER

<400> SEQUENCE: 32
gacacggccg tytattactg trmtgccnnk nnknnknnkn nknnknnknn knnknnknnk     60
nnknnknnkt actggggcca ggggacccak gtc                                  93

<210> SEQ ID NO 33
<211> LENGTH: 96
<212> TYPE: DNA
<213> ORGANISM: Artificial Sequence
<220> FEATURE:
<221> NAME/KEY: UNSURE
<222> LOCATION: 28, 29, 31, 32, 34, 35, 37, 38, 40, 41, 43, 44, 46, 47,
      49, 50, 52
<222> LOCATION: 53, 55, 56, 58, 59, 61, 62, 64, 65, 67, 68, 70, 71
<223> OTHER INFORMATION: any
<223> OTHER INFORMATION: Description of Artificial Sequence: PRIMER

<400> SEQUENCE: 33

```
gacacggccg tytattactg trmtgccnnk nnknnknnkn nknnknnknn knnknnknnk      60
nnknnknnkn nktactgggg ccaggggacc cakgtc                                96
```

<210> SEQ ID NO 34
<211> LENGTH: 99
<212> TYPE: DNA
<213> ORGANISM: Artificial Sequence
<220> FEATURE:
<221> NAME/KEY: UNSURE
<222> LOCATION: 28, 29, 31, 32, 34, 35, 37, 38, 40, 41, 43, 44, 46, 47,
      49, 50, 52
<222> LOCATION: 53, 55, 56, 58, 59, 61, 62, 64, 65, 67, 68, 70, 71, 73,
      74
<223> OTHER INFORMATION: any
<223> OTHER INFORMATION: Description of Artificial Sequence: PRIMER

<400> SEQUENCE: 34

```
gacacggccg tytattactg trmtgccnnk nnknnknnkn nknnknnknn knnknnknnk      60
nnknnknnkn nknnktactg gggccagggg acccakgtc                             99
```

<210> SEQ ID NO 35
<211> LENGTH: 102
<212> TYPE: DNA
<213> ORGANISM: Artificial Sequence
<220> FEATURE:
<221> NAME/KEY: UNSURE
<222> LOCATION: 28, 29, 31, 32, 34, 35, 37, 38, 40, 41, 43, 44, 46, 47,
      49, 50, 52
<222> LOCATION: 53, 55, 56, 58, 59, 61, 62, 64, 65, 67, 68, 70, 71, 73,
      74, 76, 77
<223> OTHER INFORMATION: any
<223> OTHER INFORMATION: Description of Artificial Sequence: PRIMER

<400> SEQUENCE: 35

```
gacacggccg tytattactg trmtgccnnk nnknnknnkn nknnknnknn knnknnknnk      60
nnknnknnkn nknnknnkta ctggggccag gggacccakg tc                        102
```

<210> SEQ ID NO 36
<211> LENGTH: 105
<212> TYPE: DNA
<213> ORGANISM: Artificial Sequence
<220> FEATURE:
<221> NAME/KEY: UNSURE
<222> LOCATION: 28, 29, 31, 32, 34, 35, 37, 38, 40, 41, 43, 44, 46, 47,
      49, 50, 52
<222> LOCATION: 53, 55, 56, 58, 59, 61, 62, 64, 65, 67, 68, 70, 71, 73,
      74, 76, 77
<222> LOCATION: 79, 80
<223> OTHER INFORMATION: any
<223> OTHER INFORMATION: Description of Artificial Sequence: PRIMER

<400> SEQUENCE: 36

```
gacacggccg tytattactg trmtgccnnk nnknnknnkn nknnknnknn knnknnknnk      60
nnknnknnkn nknnknnknn ktactggggc caggggaccc akgtc                     105
```

<210> SEQ ID NO 37
<211> LENGTH: 108
<212> TYPE: DNA
<213> ORGANISM: Artificial Sequence
<220> FEATURE:
<221> NAME/KEY: UNSURE
<222> LOCATION: 28, 29, 31, 32, 34, 35, 37, 38, 40, 41, 43, 44, 46, 47,
      49, 50, 52
<222> LOCATION: 53, 55, 56, 58, 59, 61, 62, 64, 65, 67, 68, 70, 71, 73,
      74, 76, 77
<222> LOCATION: 79, 80, 82, 83
<223> OTHER INFORMATION: any -continued
<223> OTHER INFORMATION: Description of Artificial Sequence: PRIMER

<400> SEQUENCE: 37
gacacggccg tytattactg trmtgccnnk nnknnknnkn nknnknnknn knnknnknnk    60
nnknnknnkn nknnknnknn knnktactgg ggccagggga cccakgtc    108

<210> SEQ ID NO 38
<211> LENGTH: 111
<212> TYPE: DNA
<213> ORGANISM: Artificial Sequence
<220> FEATURE:
<221> NAME/KEY: UNSURE
<222> LOCATION: 28, 29, 31, 32, 34, 35, 37, 38, 40, 41, 43, 44, 46, 47,
      49, 50, 52
<222> LOCATION: 53, 55, 56, 58, 59, 61, 62, 64, 65, 67, 68, 70, 71, 73,
      74, 76, 77
<222> LOCATION: 79, 80, 82, 83, 85, 86
<223> OTHER INFORMATION: any
<223> OTHER INFORMATION: Description of Artificial Sequence: PRIMER

<400> SEQUENCE: 38
gacacggccg tytattactg trmtgccnnk nnknnknnkn nknnknnknn knnknnknnk    60
nnknnknnkn nknnknnknn knnknnktac tggggccagg ggacccakgt c    111

<210> SEQ ID NO 39
<211> LENGTH: 114
<212> TYPE: DNA
<213> ORGANISM: Artificial Sequence
<220> FEATURE:
<221> NAME/KEY: UNSURE
<222> LOCATION: 28, 29, 31, 32, 34, 35, 37, 38, 40, 41, 43, 44, 46, 47,
      49, 50, 52
<222> LOCATION: 43, 55, 56, 58, 59, 61, 62, 64, 65, 67, 68, 70, 71, 73,
      74, 76, 77
<222> LOCATION: 79, 80, 82, 83, 85, 86, 88, 89
<223> OTHER INFORMATION: any
<223> OTHER INFORMATION: Description of Artificial Sequence: PRIMER

<400> SEQUENCE: 39
gacacggccg tytattactg trmtgccnnk nnknnknnkn nknnknnknn knnknnknnk    60
nnknnknnkn nknnknnknn knnknnknnk tactggggcc aggggaccca kgtc    114

METHOD FOR PRODUCING ANTIBODY FRAGMENTS

This is a divisional of U.S. application(s) Application Ser. No. 09/487,253, filed Jan. 19, 2000, now U.S. Pat. 6,399,763, which claims priority to European Application No. 99300351.6, filed Jan. 19, 1999 and which are incorporated herein by reference in their entirety.

FIELD OF THE INVENTION

The present invention relates to an expression library comprising a repertoire of nucleic acid sequences derived from the natural sequence repertoire but modified to enhance the extent of sequence variability, each said nucleic acid sequence encoding at least part of a variable domain of a heavy chain derived from an immunoglobulin naturally devoid of light chains and its use in producing antibodies, or more particularly fragments thereof.

In particular, the invention relates to a method for the preparation of antibodies or fragments thereof, having binding specificity for a target antigen which avoids the need for the donor previously to have been immunised with the target antigen.

BACKGROUND TO THE INVENTION

Monoclonal antibodies, or binding fragments thereof, have traditionally been prepared using hybridoma technology (Kohler and Milstein, 1975, Nature 256, 495). More recently, the application of recombinant DNA methods to generating and expressing antibodies has found favour. In particular, interest has concentrated on combinatorial library techniques with the aim of utilising more efficiently the antibody repertoire.

The natural immune response in vivo generates antigen-specific antibodies via an antigen-driven recombination and selection process wherein the initial gene recombination mechanism generates low specificity, low-affinity antibodies. These clones can be mutated further by antigen-driven hypermutation of the variable region genes to provide high specificity, high affinity antibodies.

Approaches to mimicking the first stage randomisation process which have been described in the literature include those based on the construction of 'naive' combinatorial antibody libraries prepared by isolating panels of immunoglobulin heavy chain variable (VH) domains and recombining these with panels of light variable chains (VL) domains (see, for example, Gram et al, Proc. Natl. Acad. Sa, USA, 89, 3576–3580, 1992). Naive libraries of antibody fragments have been constructed, for example, by cloning the rearranged V-genes from the IgM RNA of B cells of un-immunised donors isolated from peripheral blood lymphocytes, bone marrow or spleen cells (see, for example, Griffiths et al, EMBO Journal, 12(2), 725–734, 1993, Marks et al, J. Mol. Biol., 222, 581–597, 1991). Such libraries can be screened for antibodies against a range of different antigens.

In combinatorial libraries derived from a large number of VH genes and VL genes, the number of possible combinations is such that the likelihood that some of these newly formed combinations will exhibit antigen-specific binding activity is reasonably high provided that the final library size is sufficiently large. Given that the original B-cell pairings between antibody heavy and light chain, selected by the immune system according to their affinity of binding, are likely to be lost in the randomly, recombined repertoires, low affinity pairings would generally be expected. In line with expectations, low affinity antibody fragments (Fabs) with $K_a$s of $10^4$–$10^5$ M$^{-1}$ for a progesterone-bovine serum albumin (BSA) conjugate have been isolated from a small ($5\times10^6$) library constructed from the bone marrow of non-immunised adult mice (Gram et al, see above).

Antibody fragments of higher affinity ($K_a$s of $10^6$–$10^7$ M$^{-1}$ range) were selected from a repertoire of $3\times10^7$ clones, made from the peripheral blood lymphocytes of two healthy human volunteers (Marks et al, see above) comprising heavy chain repertoires of the IgM (naive) class. These were combined with both Lamda and Kappa light chain sequences, isolated from the same source. Antibodies to more than 25 antigens were isolated from this library, including self-antigens (Griffiths et al, see above) and cell-surface molecules (Marks et al, Bio/Technology, 11, 1145–1149, 1993).

The second stage of the natural immune response, involving affinity maturation of the selected specificities by mutation and selection has been mimicked in-vitro using the technique of random point mutation in the V-genes and selecting mutants for improved affinity.

Recently, the construction of a repertoire of $1.4\times10^{10}$ scFv clones, achieved by 'brute force' cloning of rearranged V genes of all classes from 43 non-immunised human donors has been reported (Vaughan et al 1996) and Griffiths et al, see above. Antibodies to seven different targets (including toxic and immunosuppressant molecules) were isolated, with measured affinities all below 10 nM.

The main limitation in the construction of combinatorial libraries is their size, which consequently limits their complexity. Evidence from the literature suggests that there is a direct link between library size and diversity and antibody specificity and affinity (see Vaughan et al, Nature Biotechnology, 14, 309–314, 1996), such that the larger (and more diverse) the library, the higher the affinity of the selected antibodies.

The optimisation of binding affinity through random recombination of a heavy and light chain in combinatorial libraries is complicated by sequence variations in the two framework regions, (i.e. the parts of the variable domains that serve as a scaffold in supporting the regions of hypervariability which are in turn termed the complementary determining regions or CDRs.

Only some combinations of framework sequences are compatible with the folding and interaction required for the correct orientation of the 6 CDRs that is necessary for good binding affinity. Consequently, conventional combinatorial libraries are likely to contain a high percentage of molecules that are non-functional.

The affinity of antibodies may also be improved by the process of "chain shuffling", whereby a single heavy or light chain is recombined with a library of partner chains (Marks et al, Bio/Technology, 10, 779–782, 1992).

EP-A-0368684 (Medical Research Council) discloses the construction of expression libraries comprising a repertoire of nucleic acid sequences each encoding at least part of an immunoglobulin variable domain and the screening of the encoded domains for binding activities. It is stated that repertoires of genes encoding immunoglobulin variable domains are preferably prepared from lymphocytes of animals immunised with an antigen. The isolation of single VH domains having antigen binding activities, facilitated by immunisation, is exemplified (see Example 6).

These results illustrate that although the VH part alone of a classical antibody binding domain can exhibit binding activity, the specificity and affinity are generally very low.

This may be explained by the absence of the functional involvement of the missing light chain such that only half of the intended binding pocket is present, leading to binding with related or homologous targets.

EP-A-0368684 further describes the cloning of heavy chain variable domains with binding activities generated by mutagenesis of one or each of the CDRs. The preparation of a repertoire of CDR3s is described by using "universal" primers based in the flanking sequences, and likewise repertoires of other CDRs singly or in combination. These synthetic mutant VH clones can then be recombined with VL chains to produce a synthetic combinatorial library.

Construction of libraries by such synthetic recombinatorial techniques produces a repertoire of molecules that collectively exhibit a good degree of binding diversity, wherein the variability is focussed into the sequences that encode the CDRs of each chain. However this technique does not overcome the problems previously discussed with respect to random recombination of heavy and light chains and production of non-functional molecules. Furthermore there are still six separate regions (3 CDRs in VH and another 3 in VL) determining the binding capacity of the molecule hence the repertoire of possible binding variants is encoded within a rather diffuse stretch of coding sequence, thus making a focussed approach to altering the binding affinity of these binding domains very difficult.

There remains a continuing need for the development of improved methods for constructing libraries of immunoglobulin binding domains. In particular, it would be desirable to avoid the recombination of heavy and light chains thereby preventing the formation of molecules that are non-functional following recombination.

It would also be an advantage to reduce the number of hypervariable residues in the binding domain as this would allow a more complete repertoire of possible binding variants to be obtained.

WO 94/4678, Casterman et al, describes immunoglobulins capable of exhibiting the functional properties of conventional (four-chain) immunoglobulins but which comprise two heavy polypeptide chains and which furthermore are devoid of light polypeptide chains. Fragments of such immunoglobulins, including fragments corresponding to isolated heavy chain variable domains or to heavy chain variable domain dimers linked by the hinge disulphide are also described. Methods for the preparation of such antibodies or fragments thereof on a large scale comprising transforming a mould or yeast with an expressible DNA sequence encoding the antibody or fragment are described in patent application WO 94/25591 (Unilever).

The immunoglobulins described in WO 94/4678, which may be isolated from the serum of Camelids, do not rely upon the association of heavy and light chain variable domains for the formation of the antigen-binding site but instead the heavy polypeptide chains alone naturally form the complete antigen binding site. These immunoglobulins, hereinafter referred to as "heavy-chain immunoglobulins" are thus quite distinct from the heavy chains derived from conventional (four-chain) immunoglobulins. Heavy chains from conventional immunoglobulins contribute part only of the antigen-binding site and require a light chain partner, forming a complete antigen binding site, for optimal antigen binding.

As described in WO 94/4678, heavy chain immunoglobulin $V_H$ regions isolated from Camelids (hereinafter VHH domains) which form a complete antigen binding site and thus constitute a single domain binding site differ from the $V_H$ regions derived from conventional four-chain immunoglobulins in a number of respects, notably in that they have no requirement for special features for facilitating interaction with corresponding light chain domains. Thus, whereas in conventional (four-chain) immunoglobulins the amino acid residue involved in the $V_H/V_L$ interaction is highly conserved and generally apolar leucine, in Camelid derived $V_H$ domains this is replaced by a charged amino acid, generally arginine. It is thought that the presence of charged amino acids at this position contributes to increasing the solubility of the camelid derived $V_H$. A further difference which has been noted is that one of the CDRs of the heavy chain immunoglobulins of WO 94/4678, the $CDR_3$, may contain an additional cysteine residue associated with a further additional cysteine residue elsewhere in the variable domain. It has been suggested that the establishment of a disulphide bond between the $CDR_3$ and the remaining regions of the variable domain could be important in binding antigens and may compensate for the absence of light chains.

cDNA libraries composed of nucleotide sequences coding for a heavy-chain immunoglobulin and methods for their preparation are disclosed in WO 94/4678. It is stated that these immunoglobulins have undergone extensive maturation in vivo and the V region has naturally evolved to function in the absence of the light chain variable domain. It is further suggested that in order to allow for the selection of antibodies having specificity for a target antigen, the animal from which the cells used to prepare the library are obtained should be pre-immunised against the target antigen. No examples of the preparation of antibodies are given in the specification of WO 94/4678. The need for prior immunisation is also referred to in Arabi Ghahroudi et al (FEBS Letters, 414, (1997), 521–526).

Davies et al (Bio/Technology, 13, 475–479, 1995) describe an approach to the construction of a library of binding domains based on a modified human $V_H$ domain which is intended to mimic a camelid VHH domain. This method involves replacement of the sequence segment encoding one of the CDRs by random, synthetic sequences. Although it was possible to isolate domains with selected antigen binding properties from the resulting library, these were generally characterised by poor binding affinity and specificity for protein antigens. The results would not seem, therefore, to recommend the further application of this type of approach.

The present invention relates to an expression library comprising a repertoire of synthetic or semi-synthetic nucleic acid sequences, not cloned from an immunised source, wherein said nucleic acid sequences are derived from immunoglobulins that are naturally devoid of light chains.

SUMMARY OF THE INVENTION

This invention is based on the unexpected finding that high affinity, high specificity antibodies or fragments thereof capable of binding either to protein or small molecule antigens can be obtained from a non-immunised camelid source provided that random mutagenesis of one or more CDRs is carried out, or that alternative combinations of existing CDRs are generated, in order to increase the extent of sequence variability in the antibody repertoire.

The present invention therefore provides an expression library comprising a repertoire of nucleic acid sequences, which sequences are not cloned from an immunised source, each nucleic acid sequence encoding at least part of a variable domain of a heavy chain derived from an immunoglobulin naturally devoid of light chains wherein the extent of sequence variability in said library is enhanced compared to the corresponding naïve expression library by introducing mutations in one or more of the complementarity determining regions (CDRs) of said nucleic acid sequences or by random recombination of fragments of said nucleic acid sequences, thereby generating alternative combinations of CDR and framework sequences not naturally present in the naïve library repertoire.

BRIEF DESCRIPTION OF DRAWINGS

FIGS. 1 and 1A–1l show a schematic representation of the assembly strategy expression for the library, wherein
  Step 1 illustrates the isolation of the framework regions.
  Step 2 A–C illustrates attaching the variable CDR regions to FR2, FR3 and FR4, respectively.
  Step 3 involves linking the FR1 to the CDR1-FR2 encoding fragments.
  Step 4 involves linking the FR1-CDR1-FR2 to the CDR2-FR3 fragments.
  Step 5A–D depicts the final 'full length' VHH fragment assemblies.

DEFINITION OF TERMS

Figure 1:
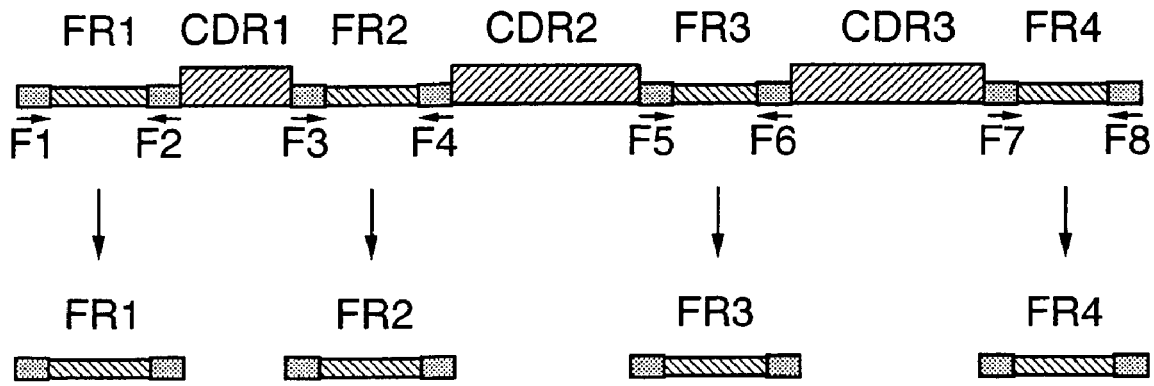

The term "naive library" refers to a collection of nucleic acid sequences encoding the naturally occurring VHH repertoire from a non-immunised source (see, Example 1).

The term "synthetic library" refers to a collection of nucleic acid sequences herein referred to as synthetic nucleic acid sequences, encoding single heavy chain antibodies or fragments thereof in which all CDR regions have undergone some form of rearrangement.

The term "semi-synthetic library" refers to a collection of nucleic acid sequences encoding single heavy chain antibodies or fragments thereof in which at least one CDR region retains natural variability and at least one CDR region has undergone some form of controlled rearrangement. Preferably in the semi-synthetic library the CDR to be randomised or mutagenised is the CDR-3.

As used herein, the term "antibody" refers to an immunoglobulin which may be derived from natural sources or synthetically produced, in whole or in part. The terms "antibody" and "immunoglobulin" are used synonymously throughout the specification unless indicated otherwise.

An "antibody fragment" is a portion of a whole antibody which retains the ability to exhibit antigen binding activity.

The term "VHH" refers to the single heavy chain variable domain antibodies of the type that can be found in Camelid mammals which are naturally devoid of light chains; synthetic and naive VHH can be construed accordingly.

The term "CDR" refers to the complementary determining region of the antibody structure.

The term "library" refers to a collection of nucleic acid sequences.

The term "repertoire," again meaning a collection, is used to indicate genetic diversity.

The term "framework region" is used herein to refer to the nucleic acid sequence regions of an antibody molecule that encode the structural elements of the molecule.

The term "anchor regions" refers to nucleic acid sequences that show homology to part of the nucleic acid sequence of the framework region or class of framework regions, such that primers based on these anchor region sequences can be used to amplify the framework regions that are present in the naive library. In the present invention the primers based on the anchor regions were able to identify at least $10^6$ different framework region sequences which could be divided into 5 different classes of fragments.

DETAILED DESCRIPTION OF THE INVENTION

The invention is based on the unexpected finding that the development of an expression library consisting of VHH domains derived from an immunoglobulin naturally devoid of light chains in which one or more of the three CDRs have been modified to enhance the extent of their sequence variability provides an effective and superior source of high affinity and high specificity antibodies, or fragments thereof when compared to conventional dual chain antibody expression libraries.

The heavy chain variable domains (VHH) for use according to the invention may be derived from any immunoglobulin naturally devoid of light chains, such that the antigen-binding capacity and specificity is located exclusively in the heavy chain variable domain.

Preferably, the heavy chain variable domains may be obtained from camelids (as described in WO 94/4678, above), especially *Lamas* (for example *Lama Glama*, *Lama Vicugia* or *Lama Paccos*) or from *Camelus* (for example *Camelus dromedaries* or *Camelus bactrionus*). Suitable sources include lymphoid cells, especially peripheral blood lymphocytes, bone marrow cells and spleen cells.

In one aspect of the invention, the framework regions of the VHH domains may conveniently be derived from a naïve library of VHH domains. This allows the natural variability in these sequence segments to be reflected in the expression library. To achieve this, the present invention has utilised information on 200 clones selected at random from a naive library of VHH. This has allowed the identification of "anchor-regions" i.e. sequences which are highly conserved within the naive clones and which are thus able to provide the basis for the design of primers capable of amplifying most if not all sequence variants of the framework regions, present in the naive library. To the extent that the framework sequences have some variability in the naïve library it is desirable also to retain this in the modified library according to the invention.

This embodiment of the invention therefore provides for the use of a naive VHH expression library derived from a non-immunised source for the construction of a synthetic or semi-synthetic VHH expression library.

Although in the present invention 200 clones have been randomly selected as a basis for framework primer design, it will be appreciated that it would be within the capacity of the person skilled in the art to design framework primers based on the homology of anchor regions with framework sequences taken from a much smaller number of clones, indeed it is not outside the capacity of the person skilled in the art to design framework primers from the sequence of a single naive cDNA clone. However, it remains the case that optimum anchor regions can most accurately be pinpointed by analysis of the homology of a large number of clones.

Therefore taking sequence homology data obtained from the randomly selected individual clones cDNA framework primers were designed (see Table 1);

i. to have sequences complementary to the anchor regions;

ii. to have a melting temperature preferably of at least 50° C., to facilitate annealing.

A large number of framework region clones could be generated in this way comprising 5 different types of fragments i.e. FR-1/FR-2A/FR-2B/FR-3/FR-4.

In another aspect of the invention, variability of the CDRs derived from the naïve repertoire is enhanced by mutation of at least some of the residues they comprise. Preferably this process introduces regions of random sequence into at least some of the CDRs. According to a particular embodiment, the CDR sequence in each individual clone is replaced by a synthetic nucleic acid sequence. Conveniently, the mutagenesis of the CDRs may be achieved by the method of overlap extension using primers which contain at each end sequences that are complementary or homologous to the anchor regions that form the basis of the framework region primers listed in Table 1 and, in between, random or partly random sequences that will ultimately encode the CDR regions. The nucleic acid sequences of the synthetically modified CDR primers are listed in Table 2.

It is important when designing the CDR primers also to take into account sequence homology within the CDR regions which was observed in the sequence data from the naive clones, as the amino acids concerned are thought to play a structural role in the VHH. It is desirable. that highly conserved sequences within the CDRs, that is, residues that are conserved amongst a substantial proportion of the VHH domains in the naïve repertoire, should be retained in the synthetically modified primers, and excluded as targets for mutagenesis.

Splicing by overlap extension follows: This is a modification of the polymerase chain reaction which has been used to generate gene fusions at very specific positions. It is based on the ability to fuse and amplify two DNA fragments containing homologous sequences i.e. 'anchors' around the fusion point.

Figure 1A:
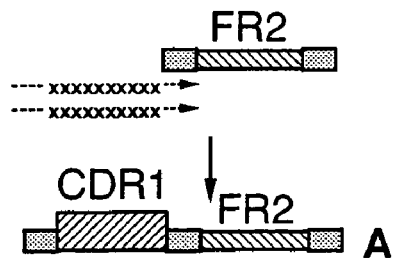
Figure 1A:
Figure 1B:
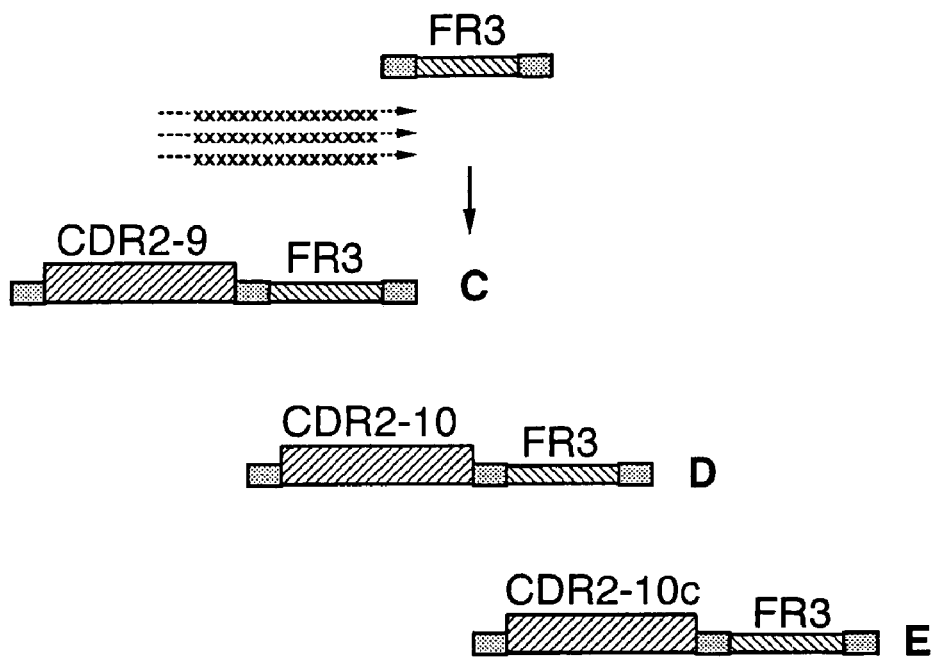
Figure 1C:
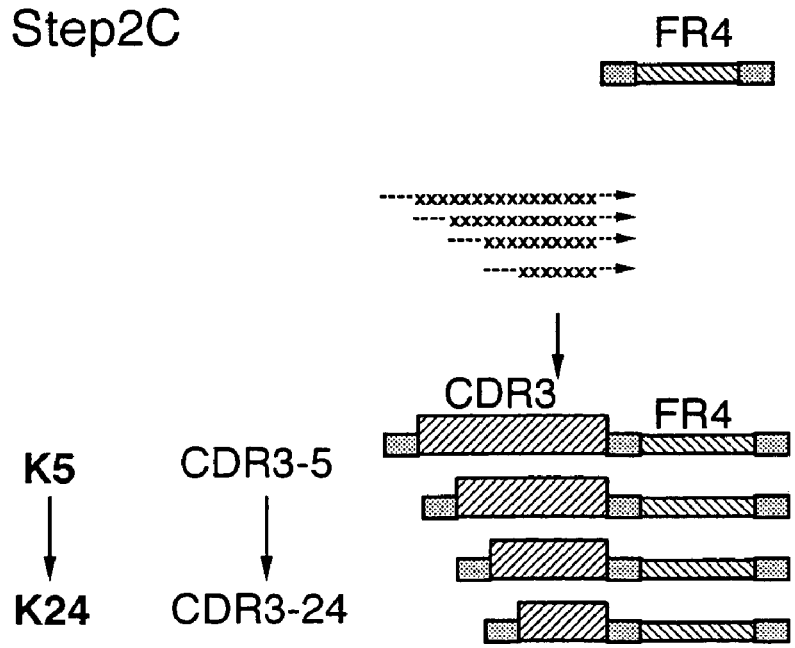
Figure 1D:
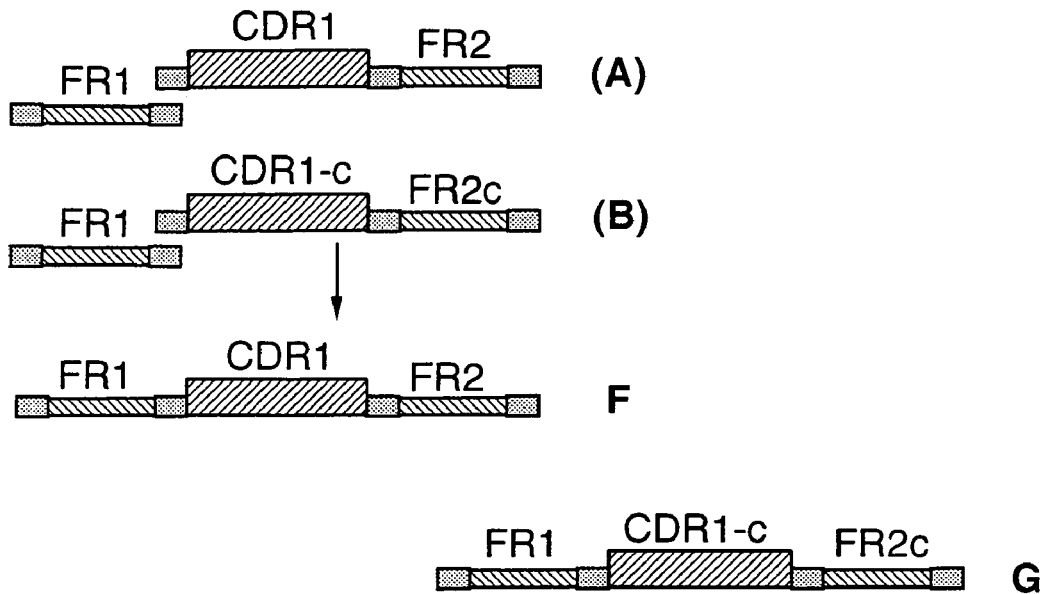
Figure 1E:
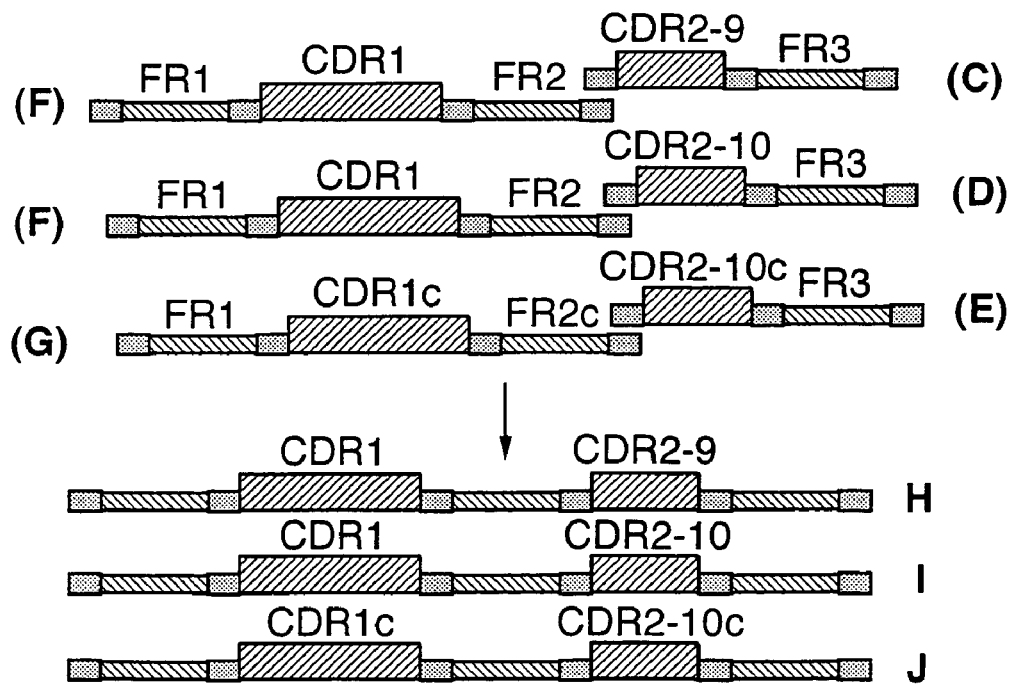
Figure 1F:
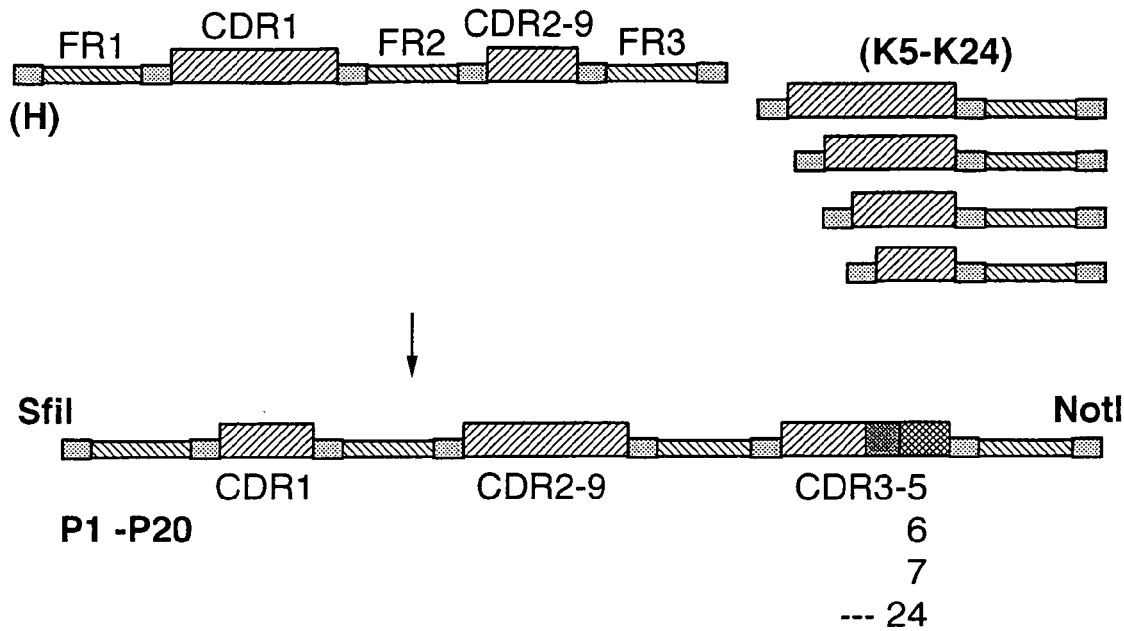
Figure 1G:
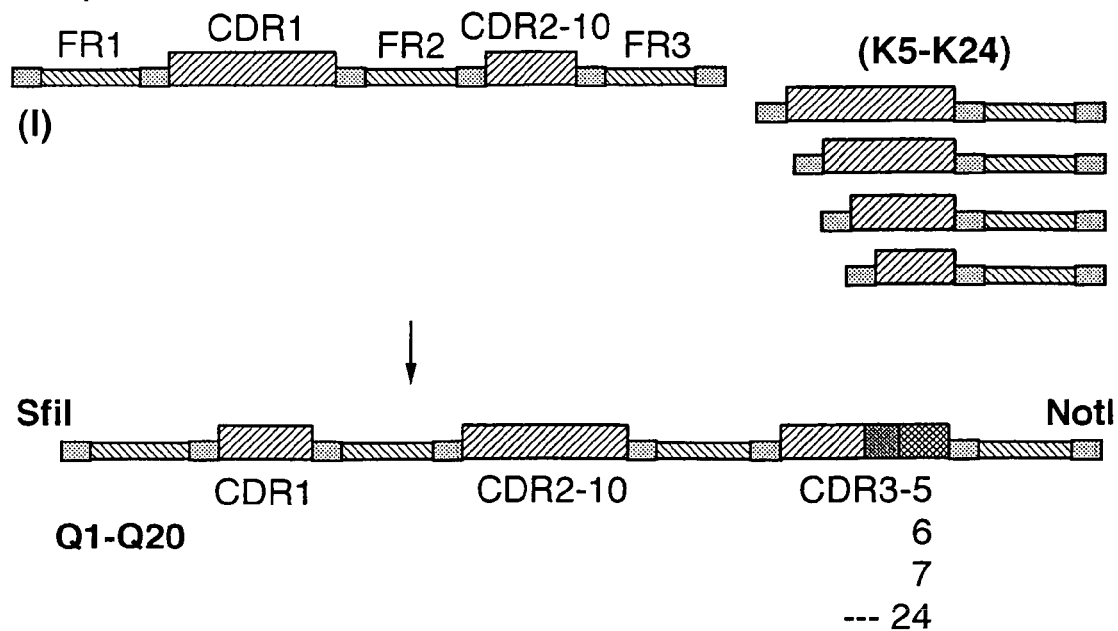
Figure 1H:
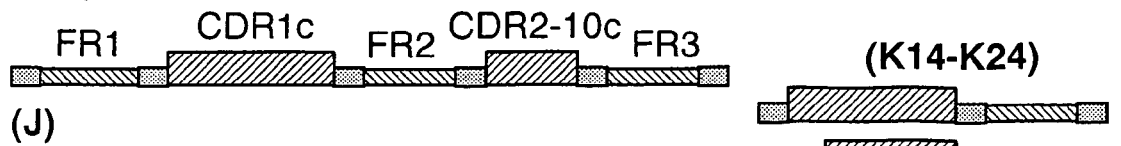
Figure 1H:
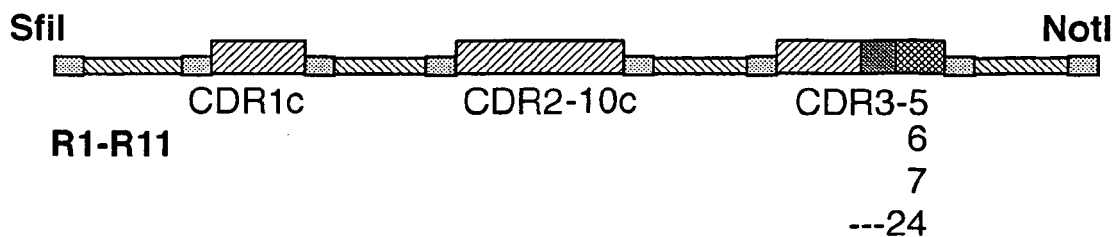
Figure 1I:
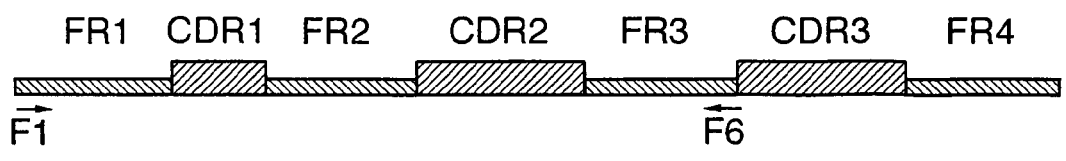
Figure 1I:
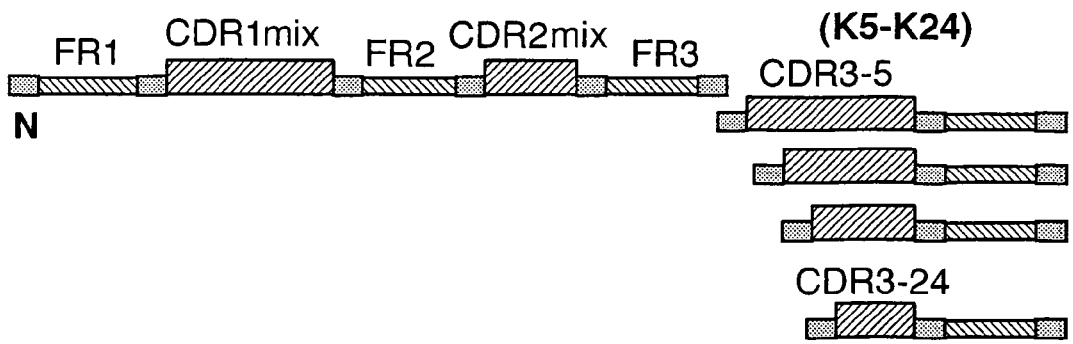
Figure 1I:

For the preparation of a 'synthetic' expression library, CDR primers incubated with framework region fragments will anneal at their complementary ends and fuse to generate randomised framework-CDR encoding fragments (see FIGS. 1A, 1B and 1C, steps 2A, B, C). This process yields CDR-1/FR-2, CDR-2/FR-3 and CDR-3/FR-4 fusion fragments. Two of these fragments are then fused (see FIGS. 1E–1l, step 3), and so forth (steps 4 and 5).

There then follows a denaturation step after which the fragments can be further annealed at the 'anchor-regions' and extended yielding the fused, double stranded gene product. If required this reaction can be followed by the PCR reaction amplifying the quantity of fused gene material. This method can easily be extended to fuse three or more fragments.

Splicing by overlap extension allows the linking of the fusion fragments at specific positions to produce a fully assembled HC-V gene which can be cloned into a suitable phage display vector such as the vector pHEN.5 using restriction enzymes such as SfiI/NotI.

It will be appreciated that other methods of introducing mutations, preferably including random or partially random sequences, into the CDRs would also be applicable. Such methods include, for example, cassette mutagenesis or the use of error-prone 'mutator' strains as bacterial hosts.

In one aspect, the present invention provides the use of a naive VHH expression library, not derived from an immunised source for the construction of a synthetic VHH expression library characterised in that all CDRs undergo a degree of sequence modification.

In another aspect, only one or two of the CDRs in the heavy chain variable domain are provided with enhanced sequence variability by the introduction of random synthetic sequences. Thus for the preparation of a 'semi-synthetic' library the FR-1/CDR-1/FR-2/CDR-2/FR-3 genes from the naive library were assembled with CD-3/FR-4 fusion fragments and cloned into the phage display vector pHEN.5 as SfiI/NotI fragments.

This aspect of the invention therefore comprises the use of a naive VHH expression library derived from a non-immunised source for the construction of a semi-synthetic VHH expression library characterised in that one or two CDRs undergo a degree of sequence modification.

In a further aspect of the invention, VHH domains with alternative combinations of three CDR sequences, which would not have been present in the unmodified naive library, may be generated by random recombination of fragments of VHH domain sequences derived from a naïve library. Optionally, this recombination process may be combined with mutagenesis of one or more of the CDRs, along the lines discussed above.

A further embodiment of the present invention resides in a method of preparing an expression library as disclosed above, comprising the steps of:

(i) taking sequence data obtained from a number of cDNA clones randomly selected from a naive VHH library;

(ii) identifying a series of 'anchor regions' which show substantially conserved homology within said sequence data and on which basis framework primers with a capacity to amplify framework regions of the naive library target DNA can be constructed;

(iii) amplification from a non-immunised source of a maximal number of different framework regions using primers from step (ii);

(iv) combining the DNA sequences encoding each CDR present in the naïve library, optionally modified by mutation or replacement, at least in part, by synthetic sequences, with framework primers showing anchor region homology to form a range of CDR primers;

(v) assembling nucleic acid sequences to create a VHH repertoire by random recombination of the range of CDR primers with the amplified framework regions using a technique of splicing by overlap extension allowing fragment fusion at the annealing anchor regions.

In another aspect, the invention provides a method for the preparation of antibody fragments derived from a non-immunised source having specificity for a target antigen comprising screening an expression library as set forth above for antigen binding activity and recovering antibody fragments having the desired specificity.

The nucleic acid sequences encoding the heavy chain variable domains for use according to the invention may conveniently be cloned into an appropriate expression vector with allows fusion with a surface protein. Suitable vectors which may be used are well known in the art and include any DNA molecule, capable of replication in a host organism, into which the nucleic acid sequence can be inserted. Examples include phage vectors, for example lambda, T4 or filamentous bacteriophage vectors such as M13. Alternatively, the cloning may be performed into plasmids, such as plasmids coding for bacterial membrane proteins or eukaryotic virus vectors.

The host cell may be prokaryotic or eukaryotic but is preferably bacterial, particularly *E coli*.

The expression library according to the invention may be screened for antigen binding activity using conventional techniques well known in the art as described, for example, in Hoogenboom, Tibtech, 1997 (15), 62–70. By way of illustration, bacteriophage displaying a repertoire of nucleic acid sequences according to the invention on the surface of the phage may be screened against different antigens by a 'panning' process (see McCatterty, Nature, 348, (1990), 552–554) whereby the heavy chain variable domains are screened for binding to immobilised antigen. Binding phage are retained, eluted and amplified in bacteria. The panning cycle is repeated until enrichment of phage or antigen is observed and individual phage clones are then assayed for binding to the panning antigen and to uncoated polystyrene by phage ELISA.

As an indication of the binding affinities of antibodies that result from the screening described in the invention; dissociation constants for the VHHs recognising a protein antigen will typically be less than 100 nM, preferably less than 75 nM, more preferred less than 50 nM, still more preferred at less than 40 nM, most preferred less than 25 nM.

The present invention therefore provides an expression library characterised in that superior binding affinity is achieved on screening than in many conventional dual chain antibody expression libraries or single domain libraries based on variable domains derived from immunoglobulins which are not naturally devoid of light chains.

The invention further provides the use of a non-immunised source of synthetic and semi-synthetic nucleic acid sequences encoding at least part of a variable domain of a heavy chain derived from an immunoglobulin naturally devoid of light chains to prepare an antibody, or fragment thereof, having binding specificity for a target antigen.

By means of the invention, antibodies, particularly fragments thereof, having a specificity for a target antigen may conveniently be prepared by a method which does not require the donor previously to have been immunised with the target antigen. The method of the invention provides an advantageous alternative to hybridoma technology, or cloning from B cells and spleen cells where for each antigen, a new library is required.

The present invention may be more fully understood with reference to the following description, when read together with the accompanying drawings.

EXAMPLE 1

Construction of the Naive VHH Library 1.1 Isolation of Gene Fragments Encoding Llama HC-V Domains A blood sample of about 200ml was taken from an non-immunised Llama and an enriched lymphocyte population was obtained via Ficoll (Pharmacia) discontinuous gradient centrifugation. From these cells, total RNA was isolated by acid guanidium thiocyanate extraction (e.g. via the method described by Chomczynnski and Sacchi, Anal. Biochem, 162, 156–159 (1987)). After first strand cDNA synthesis (e.g. with the Amersham first strand cDNA kit), DNA fragments encoding VHH fragments and part of the long or short hinge region where amplified by PCR using specific primers:

```
                       Pst I
V_H-2B    5'-AGGTSMARCTGCAGSAGTCWGG-3'                              (see SEQ. ID. NO:1)

SfiI
PCR.162: 5'-CATGCCATGACTCGCGGCCCAGCCGGCCATGGCCSAGGTSMARCTGCAGSAGTCWGG-3'  (see SEQ. ID. NO:2)
```

S=C and G, M=A and C, R=A and G, W=A and T,

```
                    HindIII     NotI
Lam-07: (see SEQ. ID. NO:3)
5'-AA-
CAGT-
TAAGCTTCCGCTTGCGGCCGCGGAGCTGGGGTCTTCGCTGTGGTGCG-3'

HindIII     NotI
Lam-08: (see SEQ. ID. NO:4)
5'-AA-
CAGT-
TAAGCTTCCGCTTGCGGCCGCTGGTTGTGGTTTTGGTGTCTTGGGTT-3'
```

Upon digestion of the PCR fragments with PstI (coinciding with codon 4 and 5 of the VHH domain, encoding the amino acids L-Q) and NotI (located at the 3'-end of the VHH gene fragments), the DNA fragments with a length between 300 and 400 bp (encoding the VHH domain, but lacking the first three and the last three codons) were purified via gel electrophoresis and isolation from the agarose gel. NotI has a recognition-site of 8 nucleotides and it is therefore not likely that this recognition-site is present in many of the created PCR fragments. However, PstI has a recognition-site of only 6 nucleotides. Theoretically this recognition-site could have been present in 10% of the created PCR fragments, and if this sequence is conserved in a certain class of antibody fragments, this group would not be represented in the library cloned as PstI-NotI fragments. Therefore, a second series of PCR was performed, in which the primary PCR product was used as a template (10 ng/reaction). In this reaction the 5 prime VH2B primer was replaced by PCR162. This primer introduces a SfiI recognition-site (8 nucleotides) at the 5 prime end of the amplified fragments for cloning. Thus, a total of 24 different PCR products were obtained, four (short and long hinge, Pst I/Not I and Sfi I/Not I) from each Llama. Upon digestion of the PCR fragments with SfiI (upstream of the HC-V coding sequence, in the pelB leader sequence) and NotI, the DNA fragments with a length between 300 and 400 bp (encoding the HC-V domain) were purified via gel electrophoresis and isolation from the agarose gel.

1.2 Construction of HCV Library in pHEN.5

The Pst I/Not I or Sfi I/Not I—digested fragments were purified from agarose and inserted into the appropriately digested pHEN.5 vector. Prior to transformation, the ligation reactions were purified by extraction with equal volumes of phenol/chloroform, followed by extraction with chloroform only. The DNA was precipitated by addition of 0.1 volume 3M NaAc pH5.2 and 3 volumes ethanol. The DNA pellets were washed×2 with 1 ml 70% ethanol, dried and resuspended in 10 μl sterile milliQ water. Aliquots were transformed into electrocompetent *E coli* XL1-Blue (Stratagene) by electroporation, using a Bio-Rad Gene Pulser. The protocol used was as recommended by Stratagene. The final library, consisting of approximately $7.8 \times 10^6$ individual clones, was harvested by scraping the colonies into 2TY+ Ampicillin (100 ug/ml)+Glucose (2% w/v) culture medium (35–50 ml each). Glycerol stocks (30% v/v) and DNA stocks were prepared from these and stored at −80° C.

EXAMPLE 2

Construction of the Synthetic VHH Library

Building on sequence data obtained from 200 individual clones randomly selected from the naive library 'anchor regions' in the framework sequences, immediately flanking the CDR regions were identified. These anchor regions were selected based on their high degree of conserved residues and the ability of primers based on these sequences to amplify most if not all of the approx. $7.8 \times 10^6$ framework regions present in the naive library.

These anchor regions are used to amplify the framework regions individually yielding 5 different types/classes of fragments (F1/F2/F2c/F3/F4). The sequences of these primers are listed in Table 1.

2.1 PCR Considerations

All PCRs for amplification of the framework building blocks and assembly of the full length VHH genes were carried out using conditions and enzymes as described in Jesperson et al (1997). The conditions chosen utilised a mixture of Taq and Pfu (2 units and 1 unit, respectively in a 100 μl reaction). The proof-reading activity of Pfu minimises the introduction of errors and, more importantly, removes the non-templated nucleotides added at the 3' terminus of PCR products amplified by Taq Polymerase. The presence of these nucleotides would result in the introduction of point mutations at the junctions of each building block in the full length VHH gene when assembled by overlap extension reactions.

2.2 Framework PCRs (F1, F2, F2c, F3 and F4)

Framework building blocks were amplified using naive library target DNA with the primers shown in Table 1. All framework and assembly DNA fragments were excised from agarose gels and purified by using the Qiaex extraction kit (Qiagen).

2.3 Assembly Reactions

CDR primers were designed on the basis of information derived from the analysis of naive library clone sequences, wherein largely conserved residues within the CDRs of such clones were assumed to perform and structural role and were maintained while sequence variability was designed in other areas.

The CDR Primers used in the construction of the VHH synthetic and semi-synthetic libraries are shown in Table 2 and a schematic representation of the assembly process is shown in FIG. 1. FIG. 2 gives an overview of the length and variability allowed in the CDR regions.

All primers used in CDR randomisation were synthesised leaving the trityl group on and full length primers were purified using cartridges and protocol supplied by Perkin Elmer. For every assembly step it was necessary to carry out 50–400 individual 100 μl amplification reactions so that after Qiaex purification, enough material was available for the next step.

Calculations of the amount of 'virgin' i.e. primary assembled non-amplified sequences required to represent all potential variability (contained within the NNKs) for the early steps in the assembly of the VHH gene were made. It was ensured that more than this amount of material was used for further amplification at each assembly step (See 1.7).

Table 3 shows the entire matrix of fragments required for both libraries. For the synthetic library 70% of the library was made up of fragment H (which contains CD2-9) assembled onto all of the CD3 primer lengths, 20% fragment I (which contained CD2-10) on all of the CD3 lengths and 10% Fragment J on the longer CD3 lengths (14–24 amino acids). The length distributions were modelled on the lengths found within the 200 randomly selected naive VHH sequences.

2.4 Initial Assemblies (A, B, C, D, E and K5 to K24)

The primers encoding the randomised CDR regions were assembled with purified Framework DNA by overlap extension reactions, using large amounts of DNA and a small number of cycles to ensure maximum yields of 'virgin' i.e. non-amplified product. Assembly of CDR Primers onto purified framework DNA (Assemblies A to E and K5 to K24) was carried out for 10 cycles with 60 ng of purified Framework DNA and 60 pmol of CDR Primer. Then a small aliquot was removed to estimate the amount of non-amplified material followed by a further 5 cycles with CDR primer (30 pmol; 1 μl) and the relevant outside primer (45 pmol; 3 μl) for each assembly (i.e. F4 for A; F4c for B; F6 for C, D and E and 170 for K5 to K24).

2.5 Initial Assemblies for the Semi-synthetic Library (N)

The fragment N (see Table 3) was amplified from target DNA (2 μl) from each of 21 naive sub-libraries using primers F1 and F6 (45 pmol in a 100 μl reaction).

2.6 Intermediate Assemblies (F, G, H, I and J)

For later assemblies F (A onto F1), G (B onto F1), H (F onto C), I (F onto D) and J (G onto E) 10 cycles of amplification were carried out using the conditions described above and 200 ng of relevant assembly and framework/assembly (see Table 3). Then a further 5 cycles were carried out with outside primers (3 μl of 15 pmol/μl (288 and F2 for F; 288 and F2c for G; 288 and F6 for H, I and J).

2.7 Final Assemblies (P5–24, Q5–24, R5–24 and S5–24)

For each assembly: 100 μl reactions were set up containing: 40–100 ng of K5 to K24 product plus 100–200 ng H, I, J, or N (ensuring excess of the larger fragment in molar terms). One to four of these reactions was carried out per required assembly, depending on amount of final product needed. The total amount of 'virgin' material in 100–400 μl total reactions was estimated and then 3 μl of each outside primer (170, 288; 15 pmol/μl) was added to each 100 μl reaction and then amplification was continued for a further 10 cycles. Yields of 'virgin' full length assembled material (before any amplification with outside primers) for all 71 fragments ranged from 40 ng to 400 ng, depending upon amounts and efficiency. This was more than sufficient to represent all potential variants as single transformants as 300 ng of a 400–500 base fragment is more than $10^{11}$ individual molecules (see Example 2.1 for the total size of the libraries).

2.8 Scale-up Amplification of Full Length VHH for Cloning

The final number of PCRs required to give the desired mixture amount for cloning of any particular fragment was calculated based on the natural distribution of CDR length and composition (Table 4). The actual mixture distribution was influenced to a certain extent by different yields obtained for different fragments.

Large-scale amplification reactions were carried out by adding 5 μl–20 μl of the first PCR reactions, (after 10 cycles overlap extension and 10 cycles outside primers) to 170/288 PCRs (~25 cycles with 2 mins elongation at 72 degrees). Total final amplifications of the 71 fragments (51 for the Synthetic library and 20 for the Semi-Synthetic library) were pooled, precipitated and run on 1% agarose gels; the full-length VHH gene product was excised and purified by Qiaex extraction. Yields after purification were approx. 1 μg per 100 μl PCR Reaction.

2.9 Construction of the VHH Libraries in pHEN.5

The 71 gel-purified DNA fragments encoding the VHH genes for the libraries were digested with SfiI (upstream of the VHH coding sequence, in the pelB leader sequence) and NotI (located at the 3'-end of the VHH gene fragments). Transformation of 100 μl of electrocompetent XL1-Blue (Strategene) E. coli with 5 μg of digested, purified pHEN.5 vector and 0.5 μg of purified, digested test fragment (close to saturation) gave approx. $8 \times 10^7$ transformants. $1000 \times 100$ μl electroporations were split between the two libraries.

The amount of purified, digested fragment was estimated for each before insertion into SfiI/NotI digested pHEN.5 and the number of ligation reactions for each fragment was calculated depending upon the amount of components in the mix. Prior to transformation, the ligation reactions were purified by extraction with equal volumes of phenol/chloroform, followed by extraction with chloroform only. The DNA was precipitated by addition of 0.1 volume 3M NaAc pH 5.2 and 3 volumes ethanol. The DNA pellets were washed×2 with 1 ml 70% ethanol, dried and resuspended in 10 μl sterile milliQ water. Aliquots were transformed into electrocompetent E. coli XL1-Blue (Stratagene) by electroporation, using a Bio-Rad Gene Pulser. The protocol used was as recommended by Stratagene.

2.10 Large-scale Phage Rescue of Synthetic VHH Libraries

The final libraries consisted of $6 \times 10^{10}$ individual clones (Synthetic library) and $4.4 \times 10^{10}$ clones (Semi-Synthetic library). The numbers of transformants for each individual fragment were calculated by pooling and titering of recovered transformants. Transformed XL1-Blue were then harvested in solution by increasing the volume of each fragment pool by 10-fold with 2TY containing Ampicillin (100 μg/ml) and Glucose (2% w/v) followed by 3 hours of growth at 37° C. with shaking. Half of this total culture volume was pooled, grown for a further 2 hours at 37° C. with shaking, spun and stored as concentrated glycerol stocks.

The remaining half of the library was diluted 2-fold with 2TY/Ampicillin/Glucose and helper phage were added.

Super-infection was allowed to occur for 30 mins at 37° C. without shaking, followed by incubation with shaking for 30 mins. The 10 liters were spun at 5000 rpm for 20 mins and the pellets were pooled. Each pellet was resusupended in 20 mls of 2TY containing Ampicillin (100 ug/ml) and Kanamycin (50 ug/ml) and pooled into one 2L flask.

The final volume was made up to 20 L with 2TY/Amp/Kan and the cultures were grown overnight, shaking at 37° C. Phage were harvested by two consecutive precipitations with 1/5 volume 20% Polyethylene Glycol 8000, 2.5 M NaCl and several aliquots were used directly for panning (see below). The remaining phage aliquots (180×1 ml for each library) were resuspended in PBS/30% glycerol and stored at −80° C.

EXAMPLE 3

Selection of VHH Fragments with Binding Affinity 3.1 Panning of the Library Using Solid Phase Immobilised Antigens Antigens Five 'antigens' were used to screen the synthetic library. These were Lactate Oxidase (LOX), Starch Branching Enzyme II (SBE II), Classical VHH antibody, a mix of Polyphenols, and Haem conjugated to Bovine Serum Albumin. Panning of phages displaying VHHs was carried out as described below.

Panning and Phage Rescue

Aliquots of phage (1 ml; $\sim 10^{13}$ phage particles resuspended in 2% Marvel [plus 2% OVA or BSA]) from the large scale phage rescue (see above) were incubated overnight with the relevant sensitised panning tubes (Nunc Maxisorb Immunosorb). Unbound phage were removed by washing the tube 20 times with PBS-T followed by 20 washes with PBS. The bound phages were eluted by adding 1 mL elution buffer (0.1M HCL/glycine pH 2.2/1 mg/mL BSA). The elution mixture was neutralised with 60 μL 2M Tris, and the eluted phages were added to 9 mL log-phase E coli XL-1 Blue. Also 4 mL log-phase E coli XL-1 Blue were added to the immunotube. After incubation at 37° C. for 30 minutes to allow infection, the 10 mL and 4 mL infected XL-1 Blue bacteria were pooled and plated onto SOBAG plates. Following growth overnight at 37° C. the clones obtained from the antigen sensitised tubes were harvested and used as starting material for the next round of panning, or alternatively individual colonies were assayed for specific antigen binding activity.

To continue panning, an aliquot (150 μl) of the overnight culture was added to 15 ml of 2TY containing Ampicillin (100 μg/ml) and Glucose (2% w/v) and allowed to grow until log-phase (A 600=0.3–0.5), at which point $4.5 \times 10^9$ pfu M13K07 helper phage were added. After infection for 30 minutes at 37° C. (without shaking) the infected cells were spun down (5000 rpm for 10 minutes) and the pellet was resuspended in 200 mL 2×TY/Amp/Kan. After incubation with shaking at 37° C. overnight, the culture was spun and the phages present in the supernatant were precipitated by adding ⅕ volume PEG/NaCl (20% Polyethylene glycol 8000, 2.5M NaCL). After incubation on ice-water for 1 hour the phage particles were pelleted by centrifugation at 8000 rpm for 30 minutes. The phage pellet was resuspended in 20 mL water and re-precipitated by adding 4 mL PEG/NaCl solution. After incubation in ice-water for 15 minutes the phage particles were pelleted by centrifugation at 5000 rpm for 15 minutes and resuspended in 2 mL PBST with 2% Marvel (plus 2% OVA or BSA). Panning results are outlined in Table 5.

EXAMPLE 4

Identification of Individual HC-V Fragments with Binding Activity

Individual bacterial colonies were picked (48 from pans 2 and 3, for all antigens) using sterile toothpicks and added to the wells of 96-well microtitre plates (Sterilin) each containing 100 μl of 2TY, 1% (w/v) glucose and ampicillin (100 mg/ml). After allowing the cultures to grow o/n at 37° C. 20 µl aliquots from each well of these 'masterplates' were added to the wells of fresh microtitre plates each containing 200 µl of 2TY, 1% glucose, 100 mg/ml ampicillin, 10^9 M13KO7 helper phage. Infection at 37° C. for 2.5 h was followed by pelleting the cells and resuspending the infected cells in 200 µl of 2TY containing ampicillin (100 mg/ml) and kanamycin (25 mg/ml). Following o/n incubation at 37° C., the phage-containing supernatants (100 µl) were added to the wells of Sterilin microtitre plates containing 100 µl/well of the appropriate blocking buffer (same buffer used as during panning reactions). Pre-blocking of the phage was carried out in these plates for 30 mins at room temp. After 30 minutes at RT, 100 µl of phage supernatant was added to the wells of a Greiner High Bind ELISA plate coated with the corresponding antigen, and to the wells of an uncoated plate. After 2 h incubation at 37° C. unbound phages were removed, and bound phages were detected with rabbit anti-M13 (in house reagent) followed by incubation with a goat anti-rabbit alkaline phosphatase conjugate. The assays were developed with 100 µl/well of p-nitrophenyl phosphate (1 mg/ml) in 1M diethanolamine, 1 mg MgCl$_2$, pH 9.6 and the plates were read after 5–10 mins at 410 nm. Results are outlined in Table 6.

EXAMPLE 5

Identification of Individual VHH Binders Using Solution Phase Panning

An alternative method has been used for the screening of the semi-synthetic library using the enzyme amylase as a target.

The antigen was biotinylated and panned using streptavidin-coated magnetic beads. High affinity binders were then selected by dropping the antigen concentration from 100 nM to 30 nM. A panel of highly specific antibody fragments were isolated and the Kd values determined using Pharmacia BiaCore SPR technology. The VHHs were captured on an NTA sensor chip via the Histidine-tag present at the C-terminus. Various concentrations (5 to 200 nM) of amylase were then passed over the sensor chip and the equilibrium constants were measured using the standard evaluation software. Results are outlined in Table 7.

TABLE 1

Framework primers

| Code | Description | Sequence |
|---|---|---|
| F1 | PelB leader | ATT GCC TAC GGC AGC CGC TG |
| F2 | 3'FR-1 | TCC AGA GGC TGC ACA GGA GA |
| F3 | 3'FR-2 | TGG T(A/T)C CGC CAG GCT CCA GG |
| F4 | 3'FR-2 | GC GAC (C/A)AA CTC GCG CT(G/C) CTT |
| F3c | 5'FR-2c | TGG TTC CGC CAG GCC CCA GG |
| F4c | 5'FR-2c | ACA TGA GAC C(C/G)C CTC (G/A)CG CTC |
| F5 | 5'FR-3 | TAT GCA GAC TCC GTG AAG GGC CG |
| F6 | 3'FR-3 | ACA GTA ATA (G/A)AC GGC CGT GTC |
| F7 | 5'FR-4 | TGG GGC CAG GGG ACC C(A/T)G GTC |
| F8 | myc-tag | TTC AGA TCC TCT TCT GAG ATG AG |

TABLE 2

CDR primers

| Code | Description | Sequence |
|---|---|---|
| CD-1 | CDR-1 (5'-3') | T(T/C) TCC TGT GCA GCC TCT GGA AG(T/C/A) A(C/T) (C/T) TT(T/C/G) AG(T/C/A) NNK NNK NNK ATG GGT TGG T(A/T)C CGC CAG GCT CCA GG |
| CD-1a | CDR-1 (5'-3') | T(T/C) TCC TGT GCA GCC TCT GGA G/T/A)TC A(C/T) (C/T) TT(T/C/G) CAT NNK TAT NNK ATT GGT TGG TTC CGC CAG GCC CCA GG |
| CD-2-9 | CDR-2 9 a.a. | AAG (C/G)AG CGC GAG TT(T/G) GTC GCA NNK ATT (T/A)CT NNK GGT GGT NNK ACA NNK TAT CCA GAC TCC GTG AAG GGC CG |
| CD-2-10 | CDR-2 10 a.a. | AAG (C/G)AG CGC GAG TT(T/G) GTC GCA NNK ATT (T/A)CT NNK NNK GGT GGT NNK ACA NNK TAT GCA GAC TCC GTG AAG GGC CG |
| CD-2-10c | CDR-2c | GAG CG(C/T) GAG G(G/C)G GTC TCA TGT TGT ATT (T/A)CT NNK NNK GAT GGT NNK ACA NNK TAT GCA GAC TCC GTG AAG GGC CG |
| CD-3-2 | CDR-3 5 a.a. | GAC ACG GCC GT(C/T) TAT TAC TGT G/A) (C/A)T GCC NNK NNK TAC TGG GGC CAG GGG ACC CA(G/T) GTC |
| CD-3-3 | CDR-3 6 a.a. | GAC ACG GCC GT(C/T) TAT TAC TGT G/A) (C/A)T GCC NNK NNK NNK TAC TGG GGC CAG GGG ACC CA(G/T) GTC |
| CD-3-4 | CDR-3 7 a.a. | GAC ACG GCC GT(C/T) TAT TAC TGT G/A) (C/A)T GCC NNK NNK NNK NNK TAC TGG GGC CAG GGG ACC CA(G/T) GTC |
| CD-3-5 | CDR-3 8 a.a. | GAC ACG GCC GT(C/T) TAT TAC TGT G/A) (C/A)T GCC NNK NNK NNK NNK NNK TAC TGG GGC CAG GGG ACC CA(G/T) GTC |
| CD-3-6 | CDR-3 9 a.a. | GAC ACG GCC GT(C/T) TAT TAC TGT G/A) (C/A)T GCC NNK NNK NNK NNK NNK NNK TAC TGG GGC CAG GGG ACC CA(G/T) GTC |
| CD-3-7 | CDR-3 10 a.a. | GAC ACG GCC GT(C/T) TAT TAC TGT G/A) (C/A)T GCC NNK NNK NNK NNK NNK NNK NNK TAC TGG GGC CAG GGG ACC CA(G/T) GTC |

TABLE 2-continued

CDR primers

| Code | Description | Sequence |
|---|---|---|
| CD-3-8 | CDR-3 11 a.a. | GAC ACG GCC GT(C/T) TAT TAC TGT G/A) (C/A)T GCC NNK NNK NNK NNK NNK NNK NNK NNK TAC TGG GGC CAG GGG ACC CA(G/T) GTC |
| CD-3-9 | CDR-3 12 a.a. | GAC ACG GCC GT(C/T) TAT TAC TGT C/A) (C/A)T GCC NNK NNK NNK NNK NNK NNK NNK NNK NNK TAC TGG GGC CAG GGG ACC CA(G/T) GTC |
| CD-3-10 | CDR-3 13 a.a. | GAC ACG GCC GT(C/T) TAT TAC TGT G/A) (C/A)T GCC NNK NNK NNK NNK NNK NNK NNK NNK NNK NNK TAC TGG GGC CAG GGG ACC CA(G/T) GTC |
| CD-3-11 | CDR-3 14 a.a. | GAC ACG GCC GT(C/T) TAT TAC TGT G/A) (C/A)T GCC NNK NNK NNK NNK NNK NNK NNK NNK NNK NNK NNK TAC TGG GGC CAG GGG ACC CA(G/T) GTC |
| CD-3-12 | CDR-3 15 a.a. | GAC ACG GCC GT(C/T) TAT TAC TGT G/A) (C/A)T GCC NNK NNK NNK NNK NNK NNK NNK NNK NNK NNK NNK NNK TAC TGG GGC CAG GGG ACC CA(G/T) GTC |
| CD-3-13 | CDR-3 16 a.a. | GAC ACG GCC GT(C/T) TAT TAC TGT G/A) (C/A)T GCC NNK NNK NNK NNK NNK NNK NNK NNK NNK NNK NNK NNK NNK TAC TGG GGC CAG GGG ACC CA(G/T) GTC |
| CD-3-14 | CDR-3 17 a.a. | GAC ACG GCC GT(C/T) TAT TAC TGT G/A) (C/A)T GCC NNK NNK NNK NNK NNK NNK NNK NNK NNK NNK NNK NNK NNK NNK TAC TGG GGC CAG GGG ACC CA(G/T) GTC |
| CD-3-15 | CDR-3 18 a.a. | GAC ACG GCC GT(C/T) TAT TAC TGT G/A) (C/A)T GCC NNK NNK NNK NNK NNK NNK NNK NNK NNK NNK NNK NNK NNK NNK NNK TAC TGG GGC CAG GGG ACC CA(G/T) GTC |
| CD-3-16 | CDR-3 19 a.a. | GAC ACG GCC GT(C/T) TAT TAC TGT G/A) (C/A)T GCC NNK NNK NNK NNK NNK NNK NNK NNK NNK NNK NNK NNK NNK NNK NNK NNK TAC TGG GGC CAG GGG ACC CA(G/T) GTC |
| CD-3-17 | CDR-3 20 a.a. | GAC ACG GCC GT(C/T) TAT TAC TGT G/A) (C/A)T GCC NNK NNK NNK NNK NNK NNK NNK NNK NNK NNK NNK NNK NNK NNK NNK NNK NNK TAC TGG GGC CAG GGG ACC CA(G/T) GTC |
| CD-3-18 | CDR-3 21 a.a. | GAC ACG GCC GT(C/T) TAT TAC TGT G/A) (C/A)T GCC NNK NNK NNK NNK NNK NNK NNK NNK NNK NNK NNK NNK NNK NNK NNK NNK NNK NNK TAC TGG GGC CAG GGG ACC CA(G/T) GTC |
| CD-3-19 | CDR-3 22 a.a. | GAC ACG GCC GT(C/T) TAT TAC TGT G/A) (C/A)T GCC NNK NNK NNK NNK NNK NNK NNK NNK NNK NNK NNK NNK NNK NNK NNK NNK NNK NNK NNK TAC TGG GGC CAG GGG ACC CA(G/T) GTC |
| CD-3-20 | CDR-3 23 a.a. | GAC ACG GCC GT(C/T) TAT TAC TGT G/A) (C/A)T GCC NNK NNK NNK NNK NNK NNK NNK NNK NNK NNK NNK NNK NNK NNK NNK NNK NNK NNK NNK NNK TAC TGG GGC CAG GGG ACC CA(G/T) GTC |
| CD-3-21 | CDR-3 24 a.a. | GAC ACG GCC GT(C/T) TAT TAC TGT G/A) (C/A)T GCC NNK NNK NNK NNK NNK NNK NNK NNK NNK NNK NNK NNK NNK NNK NNK NNK NNK NNK NNK NNK NNK TAC TGG GGC CAG GGG ACC CA(G/T) GTC |

N=G/A/T/C
K=G/T

TABLE 3

Steps in the Assembly of the Synthetic VHH Library (also see FIGS. 1 and 2)

| Assembly Name | Step Required |
|---|---|
| | Synthetic Library |
| A | CD1 onto F2 |
| B | CD1c onto F2c |
| C | CD2-9 onto F3 |
| D | CD2-10 onto F3 |
| E | CD2-10c onto F3 |
| F | CD1-F2 (A) onto F1 |
| G | CD1c-F2c (B) onto F1 |
| H | F1-CD1-F2 (F) onto CD2-9-F3 (C) |
| I | F1-CD1-F2 (F) onto CD2-10-F3 (D) |
| J | F1-CD1c-F2c (G) onto CD2-10c-F3 (E) |
| K5 to K24 | CD3-5, CD3-6, CD3-7 up to CD3-24 onto F4 |
| P5 to P24 | H onto K5 to K24 |
| Q5 to Q24 | I onto K5 to K24 |
| R5 to R24 | J onto K5 to K24 |
| | Semi-Synthetic Library |
| N | F1-CD1-F2-CD2-F3 amplified from naive library DNA using F1 and F6 |
| S5 to S24 | N onto K5 to K24 |

TABLE 4

Number of Scale-up PCRs for Final Assemblies

| | | CD 3-5 | CD 3-6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|
| Synthetic | | | | | | | | | | | | | | | | | | | | | |
| 70% | H | 5 | 5 | 10 | 30 | 50 | 55 | 60 | 70 | 80 | 85 | 90 | 85 | 70 | 55 | 40 | 20 | 10 | 10 | 5 | 5 |
| 20% | I | 5 | 5 | 5 | 10 | 10 | 15 | 20 | 20 | 25 | 30 | 25 | 20 | 15 | 10 | 10 | 5 | 5 | 5 | 5 | 5 |
| 10% | J | | | | | | | | | | 10 | 10 | 10 | 10 | 10 | 10 | 10 | 10 | 10 | 10 | 10 |
| Semi-synthetic | | | | | | | | | | | | | | | | | | | | | |
| | N | 10 | 10 | 20 | 50 | 60 | 70 | 80 | 90 | 100 | 120 | 130 | 110 | 90 | 80 | 60 | 40 | 20 | 20 | 10 | 10 |

TABLE 5

Synthetic(S) and Semi-Synthetic (SS) Library Panning Results

| Panning Antigen | Pan 1 | Pan 2 | Pan 3 | Pan 4 | Pan 5 |
|---|---|---|---|---|---|
| LOX (SS) | ND | 2-fold | 12-fold | — | — |
| SBE II (S) | ND | NONE | NONE | 8-fold | 8-fold |
| HCV-Classic (SS) | ND | 1200-fold | 10000-fold | — | — |
| Polyphenols (SS) | ND | 52-fold | 32-fold | — | — |
| Haem (SS) | ND | 500-fold | 1000-fold | — | — |

TABLE 6

Percentage of VHH phage clones which specifically recognise immobilised antigen

| Panning Antigens | Pan 2 | Pan 3 | Pan 4 | Pan 5 |
|---|---|---|---|---|
| LOX (SS) | 2% | 38% | — | — |
| SBE II (S) | 0% | 4% | 48% | 60% |
| HCV-Classical (SS) | 31% | 54% | — | — |
| Polyphenols (SS) | 23% | 9% | — | — |
| Haem (SS) | 77% | 79% | — | — |

TABLE 7

Equilibrium Constants for VHHs recognising Amylase

| VHH Number | Equilibrium Constants (nM) |
|---|---|
| 11G | 6 |
| 12A | 11 |
| 3A | 16 |
| 7E | 22 |
| 3F | 34 |
| 5F | 39 |
| 9C | 41 |

---

The invention claimed is:

1. A synthetic or semi-synthetic expression library comprising a repertoire of nucleic acid sequences derived from a naïve library repertoire and not cloned from a source immunized with a target antigen, wherein the naïve library repertoire comprising nucleic acid sequences encoding various fragments of a variable domain of a heavy chain of an immunoglobulin; each nucleic acid sequence of the expression library encoding a fragment of a variable domain of a heavy chain of an immunoglobulin devoid of light chains, wherein said heavy chain of the immunoglobulin in the expression library forms a complete antigen binding site (VHH), said fragment comprising at least the three complementarity determining regions (CDRs) and the parts of the framework that link the CDRs, wherein said expression library is produced by a method comprising the step of introducing one or more mutations in more than one of the CDRs or by shuffling nucleic acid sequences encoding CDRs and framework regions of the variable domain of the immunoglobulin heavy chain in the naïve library repertoire to generate new combinations of CDR and framework regions, the framework-CDR-encoding nucleic acid sequences in the naïve library repertoire being modified by random or partially random mutation of more than one of the CDR sequences.

2. A method for preparing antibody fragments obtained from a non-immunized source having specificity for a target antigen comprising screening the expression library of claim 1 for antigen binding activity and recovering antibody fragments having the specificity for the target antigen.

3. A synthetic or semi-synthetic VHH expression library produced by a method comprising the steps:

(i) obtaining nucleotide sequence information for a number of cDNA clones randomly selected from a naïve VHH library;

(ii) identifying a series of framework region nucleotide sequences which are conserved within the clones of the naïve VHH library;

(iii) designing framework primers based on said framework region sequences, which framework primers are capable of amplifying framework regions of cDNAs clones present in said naïve VHH library;

(iv) amplifying different framework regions of cDNA clones present in said naïve VHH library using said framework primers designed in step (iii);
(v) designing CDR primers containing nucleotide sequences that are complementary or homologous to said framework regions that form the basis of said framework primers; and
(vi) assembling randomized framework-CDR-encoding nucleic acid sequences to create a synthetic or semi-synthetic VHH repertoire by overlapping extension of randomly amplified CDR regions from said CDR primers annealed to said framework regions, the framework-CDR-encoding nucleic acid sequence being modified by random or partially random mutation of more than one of the CDR sequences.

4. The library of claim 1 or 3, wherein at least part of each of the CDR nucleic acid sequences is replaced by synthetic nucleic acid sequences such that each of said CDR nucleic acid sequences comprises random or partly random sequences.

5. The library of claim 4, wherein VHH sequences comprising alternative CDR and framework sequence combinations are generated by random recombination of fragments of VHH sequences obtained from a naïve library.

6. The library of claim 1 or 3, wherein said nucleic acid sequences are obtained from camelid immunoglobulin sequences.

* * * * *